United States Patent [19]

Murphy et al.

[11] Patent Number: 5,762,623

[45] Date of Patent: Jun. 9, 1998

[54] ELASTIC BANDAGE

[75] Inventors: Thomas S. Murphy, Boxford; Paul Taylor, North Andover, both of Mass.

[73] Assignee: Andover Coated Products, Inc., Salisbury, Mass.

[21] Appl. No.: 885,515

[22] Filed: Jun. 30, 1997

Related U.S. Application Data

[63] Continuation of Ser. No. 504,098, Jul. 19, 1995, abandoned.

[51] Int. Cl.⁶ .................................................. A61F 5/00
[52] U.S. Cl. .................................................. 602/75; 602/76
[58] Field of Search .............................. 602/41–59, 75, 602/76; 428/224, 225, 226, 229, 230; 424/443–449

[56] References Cited

U.S. PATENT DOCUMENTS

| | | |
|---|---|---|
| 2,485,725 | 10/1949 | Francis, Jr. . |
| 2,687,723 | 8/1954 | Stern . |
| 2,811,154 | 10/1957 | Scholl . |
| 3,033,201 | 5/1962 | Olsen . |
| 3,575,782 | 4/1971 | Hansen . |
| 3,763,858 | 10/1973 | Buese . |
| 4,414,970 | 11/1983 | Berry . |
| 4,653,492 | 3/1987 | Parsons . |
| 4,679,519 | 7/1987 | Linville . |
| 5,153,049 | 10/1992 | Groshens . |
| 5,209,801 | 5/1993 | Smith . |
| 5,265,445 | 11/1993 | Shytles et al. . |
| 5,297,296 | 3/1994 | Moretz et al. . |
| 5,352,216 | 10/1994 | Shiono et al. . |

FOREIGN PATENT DOCUMENTS

| | | |
|---|---|---|
| 3410169 | 9/1995 | Germany . |
| 14079 | 1/1990 | Japan . |
| 2256785 | 12/1992 | United Kingdom . |

OTHER PUBLICATIONS

Database WPI, Week 9009, Derwent Publications Ltd., London, GB; AN 90–062345 and JP 2014079 to Du Pont KK (See Abstract).

*Primary Examiner*—Richard J. Apley
*Assistant Examiner*—Kim M. Lee
*Attorney, Agent, or Firm*—Hale and Dorr LLP

[57] ABSTRACT

A laminated tape/bandage comprising a layer of transversely-spaced, longitudinally-extending elastic strands between a pair of outer layers, at least one of which is a warp-knitted (weft insertion) fabric oriented with the knit yarns extending longitudinally and generally parallel to the orientation of the elastic strands.

18 Claims, 2 Drawing Sheets

ELASTIC BANDAGE

This application is a continuation of application Ser. No. 08/504,098 filed Jul. 19, 1995, now abandoned.

This invention relates to elastic tapes and bandages and, more particularly, to disposable tapes and bandages that include a longitudinally-elastic layer laminated to an outer layer.

BACKGROUND OF INVENTION

There are in the prior art a number of disposable elastic tapes and bandages, including those sold by Conco Medical Products Co. of Rock Hill, S.C. under the trademark "MEDI-RIP", those sold by Sherwood Medical Co. of St. Louis, Mo. under the trademark "SHER-LIGHT", and those sold by Andover Coated Products, Inc. of Salisbury, Mass., the assignee of the present invention, under the registered trademark "CO-FLEX". Such bandages or tapes are typically used in sports medicine and first-aid, and also by veterinarians. The longitudinal strength of the bandage or tape is important, but it also should be relatively easy to tear to length by hand with the hand tear ability extending cleanly across the width. These latter two characteristics, particularly when coupled with the desire for a smooth neat appearance, are difficult simultaneously to obtain.

Some such bandages and tapes, such as those sold under the CO-FLEX brand, and those shown in now-expired U.S. Pat. No. 3,575,782 are a laminated structure including two outer nonwoven layers with longitudinally-extending elastic yarns sandwiched between. When the outer layers are made of light (e.g., 0.3 oz. per square yard) nonwoven nylon or polyester, such laminated bandages provide a fair appearance, but they are quite weak (longitudinal strength only about 8 pounds per inch), do not tear cleanly, and typically cannot be combined with a pressure sensitive adhesive without delaminating. Although the strength of these structures can be increased by using heavier nonwoven or film materials, this adversely affects the feel, appearance and tear characteristics of the bandage. Thus, although relatively inexpensive, these laminated structures do not provide many of the characteristics needed in a relatively strong disposable elastic tape/bandage that demonstrates good hand tear.

To provide better feel, appearance, hand tear characteristics and strength, the art has turned to products, such as the "MEDI-RIP" and "SHER-LIGHT" brand bandages, that include a woven fabric in which elastic yarns are actually woven or knitted into the fabric, usually in the long or warp direction. However, if, as in the case of the "SHER-LIGHT" bandage, such products are made using a woven fabric that is heavy enough to produce a bandage that has a longitudinal strength of more than about 10 pounds per inch, the increased weight of the woven fabric not only increases the cost, it makes the entire bandage heavier and less comfortable and also adversely affects the hand tear characteristics.

There remains a need for an inexpensive, elastic, hand tear tape or bandage that can be made either cohesive or adhesive, has a good appearance, is soft and comfortable to wear, hand tears cleanly, and that, despite its light weight and low cost, has a longitudinal strength that, on an equal weight basis, is greater than that of either woven or nonwoven tear tapes now available.

SUMMARY OF INVENTION

The present invention features a laminated tape/bandage comprising a layer that is elastic in the longitudinally-extending direction laminated to one side of a warp-knitted, sometimes referred to as warp-knitted (weft insertion), fabric oriented with the knit yarns extending longitudinally. In preferred embodiments in which the elastic layer is longitudinally-extending elastic strands laminated between a pair of outer layers, at least one of which is warp-knitted (weft insertion), the warp-knitted (weft insertion) fabric has a weight of less than about 50 grams per square meter (about 1.5 oz. per square yard) and most preferably less than about 25 to 30 grams per square meter (about 0.7 to 0.9 oz. per square yard), and the other outer layer is a lightweight spun-blown synthetic nonwoven. The complete tape/bandage has a good appearance, hand-tears cleanly transversely of the tape, has a longitudinal strength that on a weight basis is greater than that of commercially available hand-tearable woven bandage products, and is considerably less expensive than its woven or knitted competitors where the elastic yarns are woven or knitted into the fabric, as an integral part of the woven or knitted cloth.

DETAILED DESCRIPTION OF PREFERRED EMBODIMENT

Figure 1:
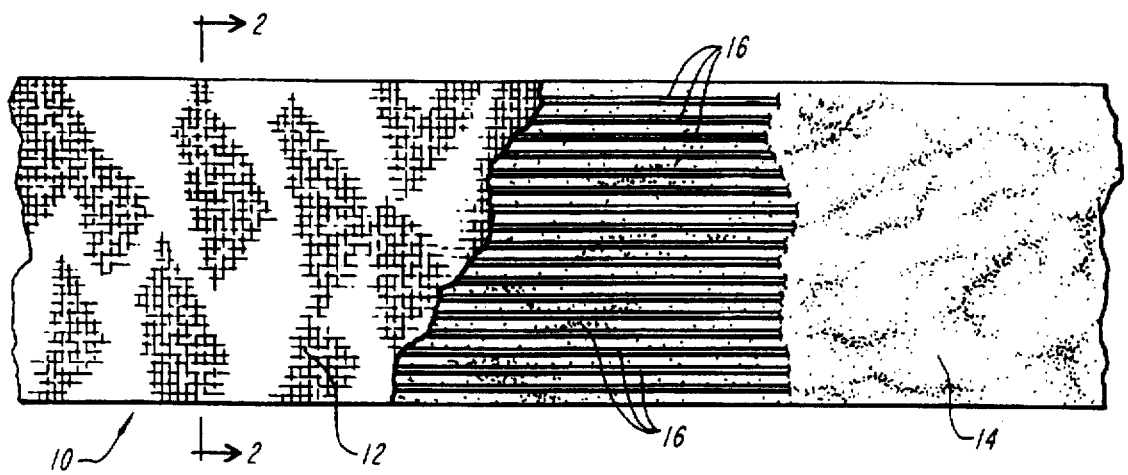
FIG. 1 is top view, partially broken away, of a tape or bandage embodying the present invention.
Figure 2:
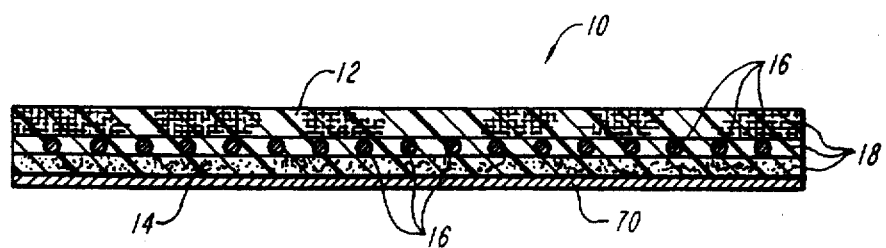
FIG. 2 is a cross-sectional view, taken at line 2—2 of FIG. 1.

FIGS. 1 and 2 illustrate a laminated tape or bandage, generally designed 10, comprising a top layer 12 of warp-knitted (weft insertion) fabric, a bottom layer 14 of spun bond nylon nonwoven, and a middle layer of longitudinally-extending, transversely spaced (about 12 per inch) elastic strands 16. The three-layer structure is laminated together with a binder 18 that impregnates all three layers.

The preferred warp-knitted (weft insertion) fabric is obtained from Welbek UK Ltd. of Nottingham, England, and is designated Welbek Technical Textiles Ref. No. P010. The fabric has a weight of about 25 grams per square meter (about 0.7 oz. per square yard), a thickness of about 0.13 millimeters, and a warp weft thread count of 18×16. The knitted warp yarns are 45 denier polyester; the 150 denier fill or weft yarns are loose, nontwisted, texturized polyester filaments. Similar warp-knitted (weft insertion) fabrics are available elsewhere, e.g., warp-knitted (weft insertion) greige fabric available from Milliken & Company of Spartenburg, S.C.

The elastic strands 16 of the preferred embodiment are 280 denier, and are sold under the trademark GLOSPAN by Globe Mfg. Co. of Fall River, Mass. Depending on the amount of elasticity desired in the finished tape/bandage 10, both the denier and number of elastic strands per inch (measured transversely) of the tape/bandage may vary. For example, the denier of the elastic strands may vary from less than 100 to about 1000, and there may be from about 5 to about 15 elastic strands per inch. Typically, the tape/bandage 10 is formed by laminating the warp-knitted (weft insertion) fabric 12, when fully-extended or taut, over stretched elastic strands 16.

The spun bond nonwoven forming the other outer layer 14 of the tape/bandage 10 is quite light typically about 10 grams per square meter (about 0.3 oz. per square yard) and no more than about 17 grams per square meter (about 0.5 oz. per square yard), and is easily obtained commercially. Polyester, cellulosic, polypropylene, etc. may be used in lieu of nylon in a spun bond nonwoven, and a light woven cotton scrim may be used also.

The particular binder 18 used to laminate the three layers together to form the finished product depends, principally, on whether and what kind of adhesive properties are desired. When, as in many applications, a cohesive (i.e., will stick only to itself) product is desired, a natural rubber base binder is employed. A 50:50 acrylic:SBR blend is employed to produce either a nonadhesive product or a product that is to be coated on one side with a pressure-sensitive adhesive. In any event, the binder 18 impregnates all three layers. A dye may be incorporated in the binder to provide any desired final color to the product, at a fraction of the cost required to dye the yarns or fabrics themselves as is necessary in prior art constructions.

The laminated tape/bandage 10 of the preferred embodiment has a strength, in the longitudinal warp direction, of about 20 pounds per inch of width; yet it is light, comfortable to wear, can easily be torn transversely by hand, and when so torn tears cleanly substantially perpendicularly across the width of the tape/bandage. As compared to the commercially available bandages made by weaving or knitting elastic yarns into a woven fabric, the laminated warp-knitted (weft insertion) bandage of the present invention provides, at a cost of production that is about half that of comparable woven tape/bandages, a hand and appearance that is at least equal and often superior, equal or superior tear characteristics, and greater longitudinal strength on both a weight and cost basis. Compared to prior art laminated products, the hand, appearance, tear characteristics, and longitudinal strength of the tape/bandage of the present invention are all superior.

Figure 3:
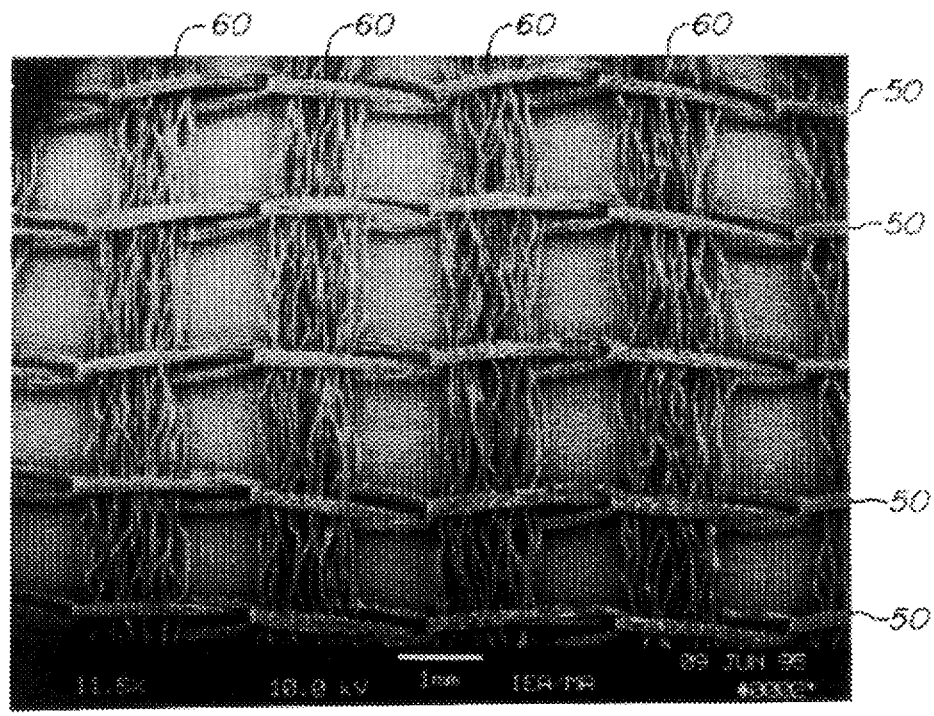
FIGS. 3 and 4 are a microscopic photographs of a warpknitted (weft insertion) fabric used as one of the layers of the tape/bandage of FIG. 1.
Figure 4:
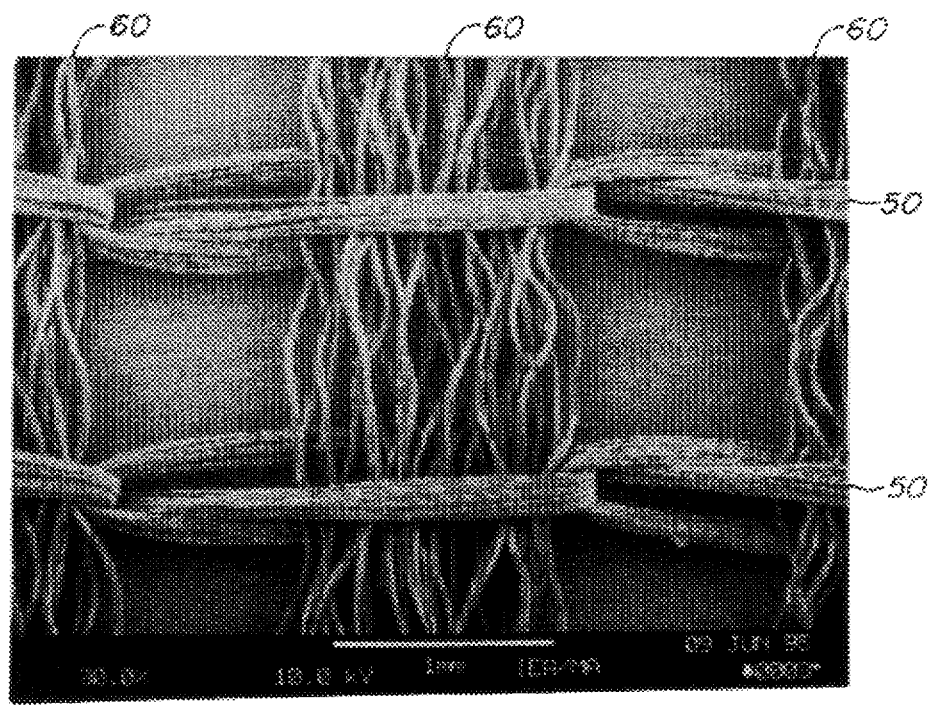

The microphotographs of FIGS. 3 and 4 show the warp-knitted (weft insertion) fabric of top layer 12 in greater detail. FIG. 3 is taken at 11.5× magnification; FIG. 4 is taken at 30× magnification. Both Figures include a 1 mm reference scale. In both Figures, the fabric is oriented so that the polyester knitted warp yarns, designated 50, extend generally from left to right, and the loose, non-twisted fill or weft yarns, designated 60, extend vertically. Because the fabric is warp knit-weft insertion rather than conventionally woven, the knitted warp yarns 50 form rather loose warp yarn "loops" around the fill yarns 60, and the knitted warp structure also provides that each row of the knitted warp includes three yarns 50 extending in the warp direction. This three-yarn warp-knitted (weft insertion) construction results in the lightweight and high tensile strength (about 21.8 lbs/inch) in the warp direction.

When the warp-knitted (weft insertion) fabric of layer 12 is fully extended in the warp direction, as shown in FIGS. 3 and 4, the space (almost 1 mm) between adjacent fill or weft yarns 60 is almost as great as the overall diameter (about 1 mm) of the fill yarns. This spacing, coupled with the loose, non-twisted, filamentary structure of the fill yarns themselves, permits the fill yarns to move towards and away from each other in response to stretch and relaxation of the longitudinal elastic strands 16, which is of course accompanied by elongation and relaxation of the warp yarns.

As shown in FIG. 2, a layer of pressure-sensitive adhesive 70 may be coated on the outside of nonwoven layer 16. For applications in which even greater strength is desired, a second layer of warp-knitted (weft insertion) fabric or scrim may be used in place of nonwoven layer 16.

Other embodiments will be within the scope of the following claims.

What is claimed is:

1. A laminated elastic tape comprising:

a first layer of warp-knitted (weft insertion) fabric having knit yarns and fill yarns and oriented with the knit yarns thereof extending longitudinally of the tape, said knit yarns being non-elastic, each of said knit yarns extending longitudinally of the tape and including a plurality of longitudinally-spaced knitted loops, and each of the fill yarns extending transversely of the tape and through loops of the knit yarns;

a second layer which is elastic in a direction extending longitudinally of the tape; and, a binder bonding said layers together.

2. The laminated tape of claim 1 wherein said second layer comprises individual elastic strands spaced transversely of the tape relative to each other and extending longitudinally of the tape.

3. The laminated tape bandage of claim 2 wherein said elastic strands have a denier less than about 1000.

4. The laminated tape bandage of claim 2 wherein said elastic strands are spaced at a density in the range of 5 to 15 per inch measured transversely of the bandage.

5. The laminated tape of claim 4 wherein said density is about 12 per inch.

6. The laminated tape of claim 1 including a third layer, said second layer being laminated between said first and third layers.

7. The laminated tape of claim 6 wherein said third layer is a synthetic spun bonded nonwoven material.

8. The laminated tape of claim 6 wherein said third layer has a weight of no more than about 0.5 oz. per square yard.

9. The laminated tape of claim 6 wherein said third layer is a spun bond nonwoven having a weight of not more than about 0.5 oz. per square yard.

10. The laminated tape of claim 6 wherein said nonwoven is selected from the group consisting of nylon, polyester and polypropylene and has a weight of not more than about 0.3 oz. per square yard.

11. The laminated tape of claim 6 wherein said binder impregnates said first, second, and third layers.

12. The laminated tape of claim 6 wherein a layer of pressure-sensitive adhesive is coated on the outer side of one of said first or third layers.

13. The laminated tape of claim 1 wherein said knit yarns of said warp-knitted (weft insertion) layer comprise polyester yarns.

14. The laminated tape of claim 13 wherein said fill yarns off said warp-knitted (weft insertion) layer comprise texturized filament yarns.

15. The laminated tape of claim 3 wherein said warp-knitted (weft insertion) layer has a weight of not more than about 1.5 ounces per square yard.

16. The laminated tape of claim 15 wherein said weight is not more than 0.9 ounces per square yard.

17. The laminated tape of claim 1 wherein a layer of pressure-sensitive adhesive is coated on the outer-side of one of said layer.

18. The laminated tape of claim 1 wherein said knit yarns are knitted such that the loops formed by the knit yarns include three yarn portions.

* * * * *

UNITED STATES PATENT AND TRADEMARK OFFICE
CERTIFICATE OF CORRECTION

PATENT NO : 5,762,623
DATED : June 9, 1998
INVENTOR(S): Murphy, Thomas S. and Taylor, Paul It is certified that error appears in the above-identified patent and that said Letters Patent are hereby corrected as shown below:

At column 4, line 22, delete "bandage".

At column 4, line 53, delete "off" and insert --of--.

At column 4, line 62, delete "layer" and insert --layers--.

Signed and Sealed this

Fourth Day of April, 2000

Q. TODD DICKINSON

*Attest:*

*Attesting Officer*        *Director of Patents and Trademarks*